United States Patent
Belogi et al.

(10) Patent No.: US 7,935,818 B2
(45) Date of Patent: May 3, 2011

(54) PROCESS FOR THE PREPARATION AND PURIFICATION OF VALGANCYCLOVIR HYDROCHLORIDE

(75) Inventors: Gianluca Belogi, Mulazzano (IT); Alessia Rossi, Mulazzano (IT); Angelo Bedeschi, Mulazzano (IT); Roberta Pizzocaro, Mulazzano (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 910 days.

(21) Appl. No.: 11/820,724

(22) Filed: Jun. 20, 2007

(65) Prior Publication Data
US 2008/0076923 A1    Mar. 27, 2008

(30) Foreign Application Priority Data

Jun. 21, 2006 (EP) .................................... 06012784

(51) Int. Cl.
*C07D 473/18* (2006.01)
(52) U.S. Cl. ....................................................... 544/276
(58) Field of Classification Search ................. None
See application file for complete search history.

(56) References Cited

U.S. PATENT DOCUMENTS

| 6,083,953 | A * | 7/2000 | Nestor et al. ............ 514/263.38 |
| 6,103,901 | A * | 8/2000 | Arzeno et al. ................. 544/276 |
| 6,340,756 | B1 * | 1/2002 | Dvorak et al. ................. 544/276 |
| 2007/0225305 | A1 * | 9/2007 | Ramchandra et al. ........ 544/276 |
| 2010/0081809 | A1 * | 4/2010 | Devarakonda et al. ....... 544/276 |

OTHER PUBLICATIONS

O'Donnell, Tetrahedron Letters vol. 40, Issue 32, Aug. 6, 1999, pp. 5831-5835.*

* cited by examiner

*Primary Examiner* — Mark L Berch
(74) *Attorney, Agent, or Firm* — Ladas & Parry LLP

(57) ABSTRACT

A process for the preparation of valgancyclovir which comprises:
a) reacting a compound of formula 7,

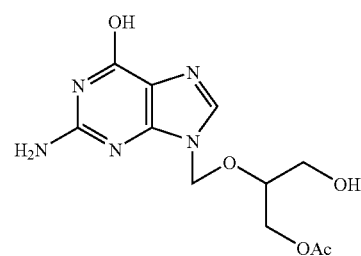

7 in an aprotic solvent, in the presence of a condensing agent, with a compound of formula 8,

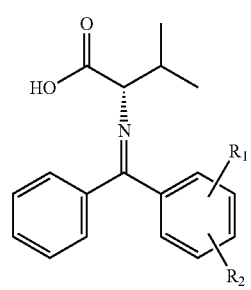

8 wherein $R_1$, and $R_2$ may be, each independently, hydrogen, an halogen atom or an hydroxyl group; the double bond may either be in the E or Z configuration or a mixture thereof to yield a compound of formula 9

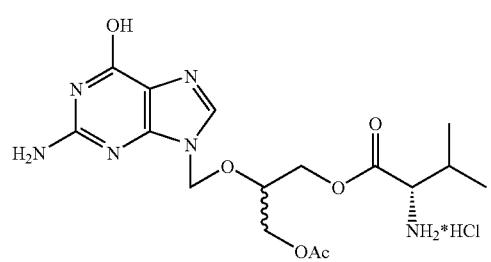

9 b) mild hydrolysis of compound obtained in a) to give valgancyclovir.

6 Claims, 7 Drawing Sheets

Figure 1: SEM picture of crystalline Valgancyclovir hydrochloride

Figure 2: SEM picture of lyophilized Valgancyclovir hydrochloride

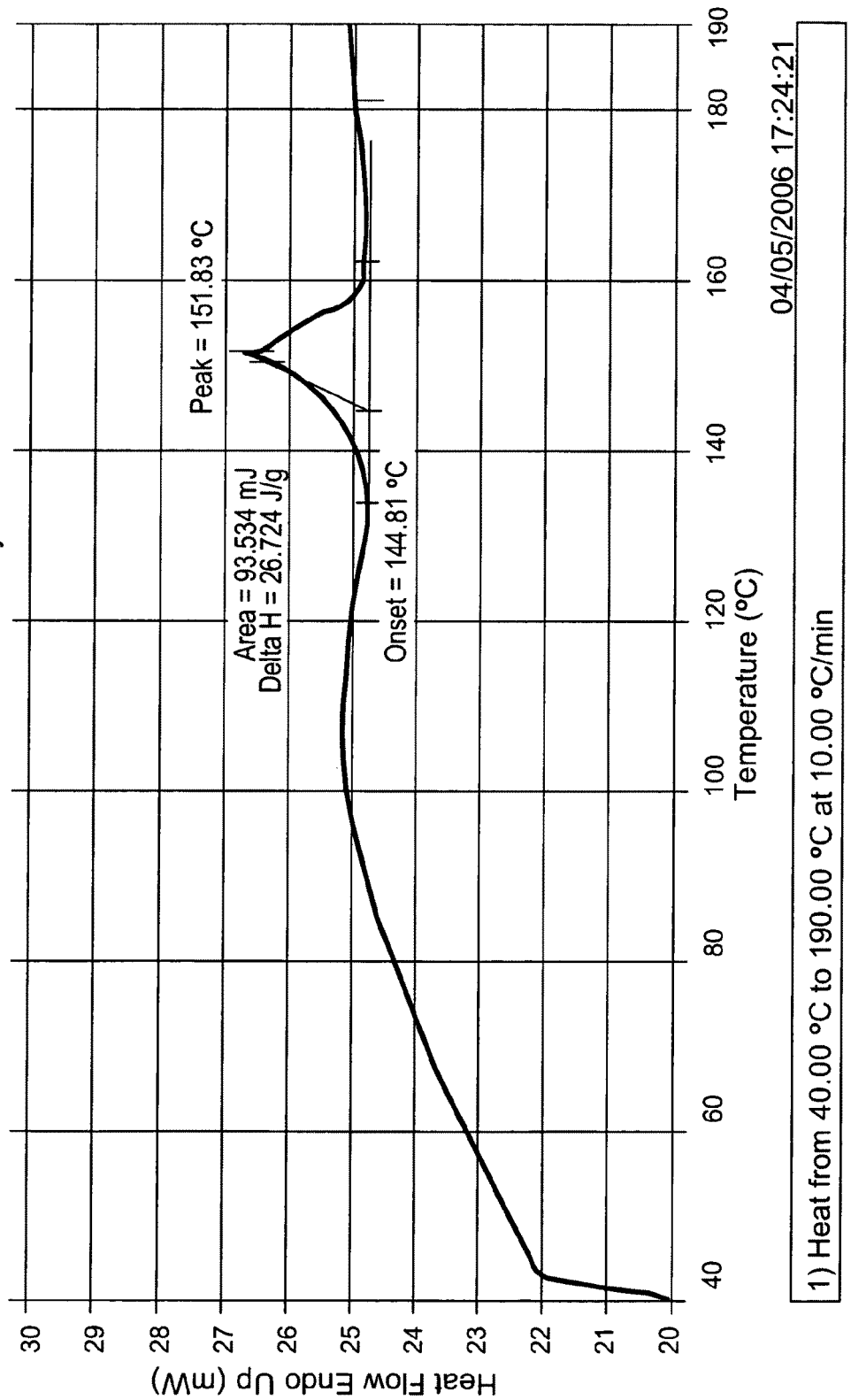

PROCESS FOR THE PREPARATION AND PURIFICATION OF VALGANCYCLOVIR HYDROCHLORIDE

FIELD OF THE INVENTION

The present invention provides a process for the preparation of Valgancyclovir hydrochloride.

BACKGROUND OF THE INVENTION

Valgancyclovir hydrochloride (formula 1) or L-valine, 2-[(2-amino-1,6-dihydro-6-oxo-9H-purin-9-yl)methoxy]-3-hydroxypropyl ester hydrochloride, is presently available as a mixture of two diastereoisomers substantially in the same amount.

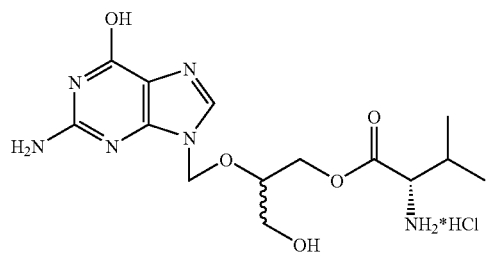

1

Valgancyclovir hydrochloride is known from EP 694547 as an antiviral agent particularly against cytomegalovirus infections.

Processes for the preparation of valgancyclovir hydrochloride are also known from U.S. Pat. No. 5,840,890, U.S. Pat. No. 5,856,481 and U.S. Pat. No. 6,083,953. The process disclosed in said patents substantially follows the synthetic path outlined in Scheme 1.

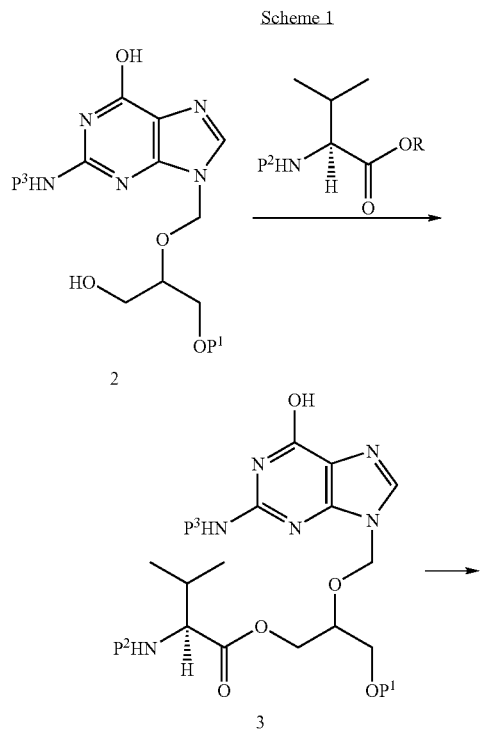

Scheme 1

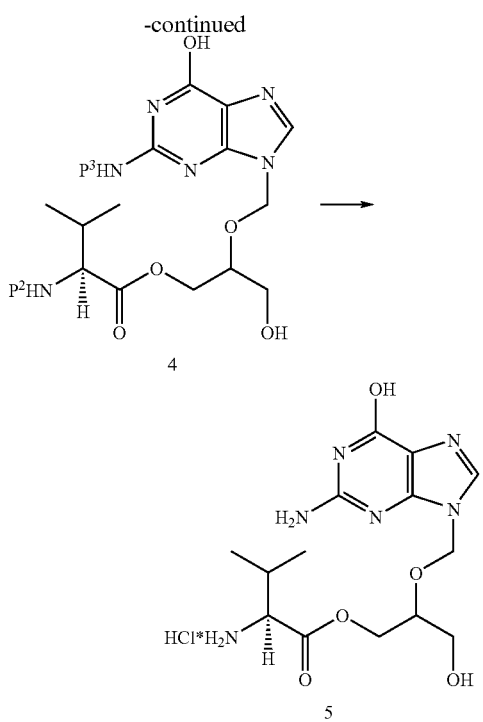

wherein $P^1$, $P^2$ and $P^3$ are well known protecting groups such as those used typically for the synthesis of peptides or, for instance, in the synthesis of Valacyclovir (EP 308 065), or other valine derivatives of gancyclovir (U.S. Pat. No. 5,043,339), e.g. trityl, acetoxy, tert-butoxycarbonyl (BOC), 9-fluorenylmethoxycarbonyl (FMOC), carbobenzoyloxy (Cbz) derivatives and the like.

This synthetic pathway is cumbersome, starting from a substrate with different reactive groups, i.e. hydroxy and amino groups, so that a good selectivity is required in the reaction steps. As described above, this problem is solved by means of protecting groups. In fact, the synthesis starts from a suitably mono-protected derivative of Gancyclovir (2), that is reacted with a suitably protected L-valine, to give compound 3. The hydroxy group protection is then removed by mild hydrolysis and eventually the valine amino protecting group is removed. Optionally, also a $P^3$ protecting group may be present and is removed by an additional step. Overall, of the three (or four, when a $P^3$ group is present) steps needed for preparing valgancyclovir hydrochloride, as shown in scheme 1, two (or three) are deprotection steps.

All these protection-deprotection sequences are of course disadvantageous and affect yields, purity of the compound and costs.

Attempts starting from an unprotected gancyclovir, reported in U.S. Pat. No. 5,700,936, result in a double addition of the L-valine moiety. Hydrolysis of one of the two valine residues affords the desired compound. This approach however yields a mixture of mono-, diesters and gancyclovir, as the hydrolysis is poorly selective. In the same area, but with a different approach, WO 2005/092891 discloses the preparation of valgancyclovir hydrochloride aiming at the selective monoacylation of gancyclovir, but this resulted again in a mixture of mono- and di-esters, plus non-reacted starting material (gancyclovir). The presence of complex mixtures requires extensive additional purifications steps and crystallizations, negatively affecting yields and operability of the process.

Also, attempts to use alternate activated valine derivatives, such as cyclic anhydride of formula 6, were also described in U.S. Pat. No. 5,700,936, U.S. Pat. No. 5,756,73 and U.S. Pat. No. 6,040,446.

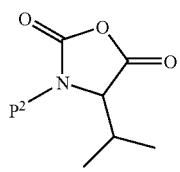

6

However, this approach did not result in an increase of synthetic efficiency, since the compound of formula 6 still needs the presence of the protecting group $P^2$ and requires anyway an additional deprotection step. In addition, the protection $P^2$ in compounds of formula 6 may only refer to N-monosubstituted protecting groups, limiting the flexibility of the process.

It would be therefore useful to avoid such protection-deprotection sequences in order to increase the overall synthetic efficiency. To this purpose, a convenient starting material should have the following advantages:

1 selective vs. other reactive groups present in the compound.
2. able to act as an unprotected L-valine equivalent so as to reduce the number of steps for the preparation of valgancyclovir.
3. commercially available, inexpensive, easy to recover and recycle without further manipulations.

In fact, in addition to the drawbacks mentioned above, the cleavage of the protecting groups usually involves the transformation of the protecting group itself, that therefore cannot be recycled giving impurities and by-products.

The solution to said problems is not easy since there is only a limited choice of compounds potentially meeting the above criteria. Schiff bases could be considered but they are known to be unstable in even mild acidic conditions, needed for the synthesis of the free acids, that are instead required for the reaction of an adduct of L-valine with the alcohol of formula 2 in the presence of a condensing agent. It has been reported by Halpern, B. et al. *Aust. J. Chem*, 1974, 27, 2047, and in *Aust. J. Chem*. 1976, 29, 1591, that ketones of formula 10, give adducts sufficiently stable to yield the free acid derivatives. Such adducts, however, react with amino groups, whereas their reaction with aliphatic alcohols has not been disclosed. In addition, compound 2 is hindered, sparingly soluble, and poorly reactive so that the hindrance of the obtained adduct itself makes it even less reactive.

DESCRIPTION OF THE INVENTION

It has now been surprisingly found that valine adducts of certain ketones react with alcohols of formula 2, with a good stereochemical control. Said valine adducts are L-valine equivalents, yielding directly the desired compound.

The purity of the obtained intermediate also allows the isolation with good purity of valgancyclovir hydrochloride, which is thus easily purified and then directly isolated from the aqueous solution by lyophilization. The invention also relates to the lyophilized form of valgancyclovir hydrochloride.

The process for the preparation of valgancyclovir hydrochloride according to the invention comprises:

a) reacting a compound of formula 7,

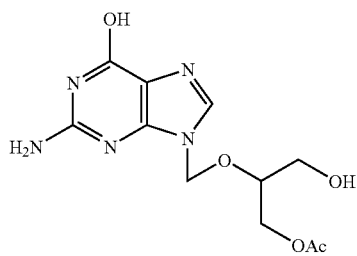

7 in an aprotic solvent, in the presence of a condensing agent, with a compound of formula 8,

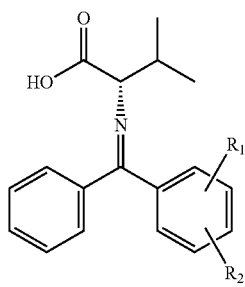

8 to yield a compound of formula 9

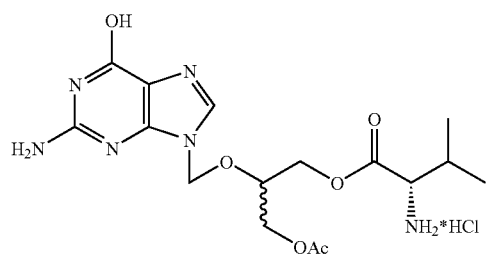

9 b) mild hydrolysis of compound obtained in a) to give valgancyclovir hydrochloride.

Valgancyclovir hydrochloride may be then isolated from the hydrolytic solution by lyophilization.

Optionally, valgancyclovir hydrochloride may be directly obtained by reacting a compound of formula 7 with a compound of formula 8, followed by mild hydrolysis.

The starting material 7 is known and may be obtained as described in U.S. Pat. No. 5,250,535, example 6B. Compound 8 is also known and may be obtained as described in Halpern, B. et al. *Aust. J. Chem*, 1974, 27, 2047, and in *Aust.*

J. Chem. 1976, 29, 1591, for instance by reaction of L-valine with a compound of formula 10.

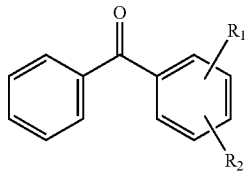

The present invention also provides a purification method allowing the removal of gancyclovir, that is formed as hydrolytic by-product and the isolation of valgancyclovir hydrochloride from an aqueous solution, preventing its degradation to gancyclovir, which is easily formed in aqueous media.

The invention accordingly provides a method for the purification and isolation of valgancyclovir hydrochloride by precipitation of gancyclovir from an aqueous solution and isolation of pure valgancyclovir hydrochloride by lyophilization. Valgancyclovir hydrochloride obtained from freeze-drying process is also new and is a further object of the invention.

BRIEF DESCRIPTION OF THE DRAWINGS

FIG. 7 DSC thermogram of lyophilized Valgancyclovir hydrochloride.

DETAILED DESCRIPTION OF THE INVENTION

Figure 1:
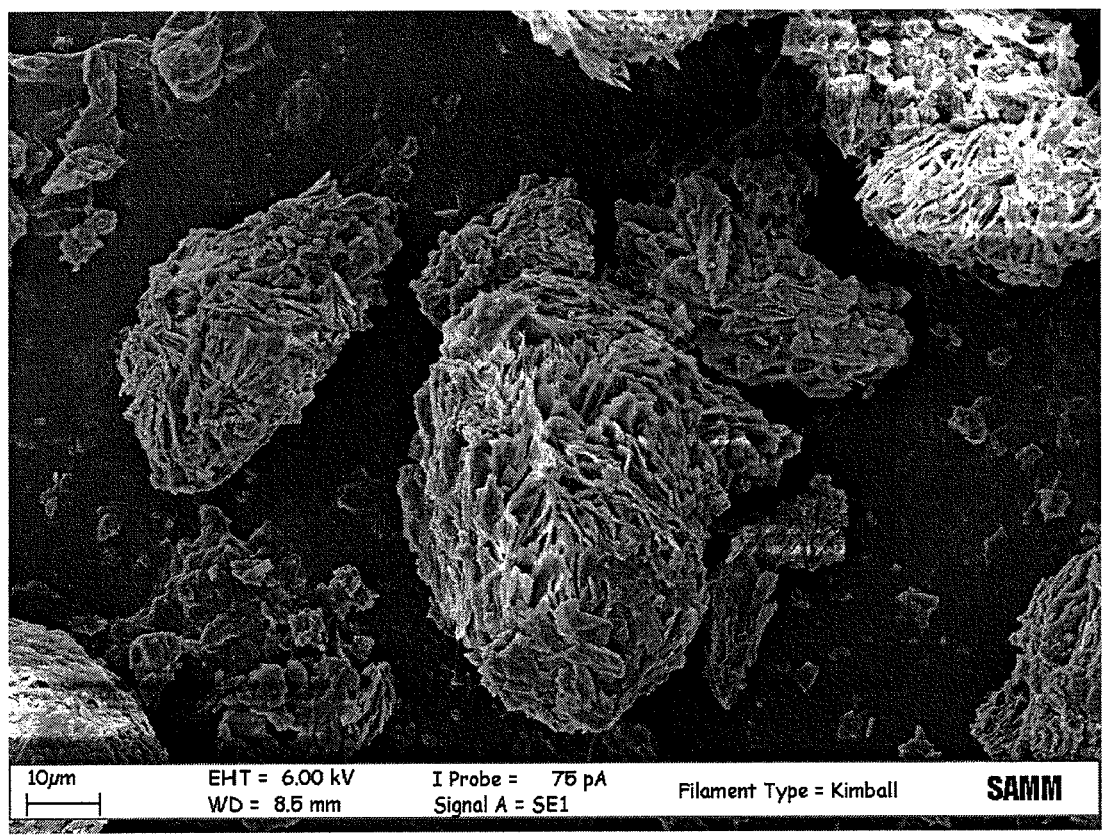
FIG. 1 SEM picture of crystalline Valgancyclovir hydrochloride.
Figure 2:
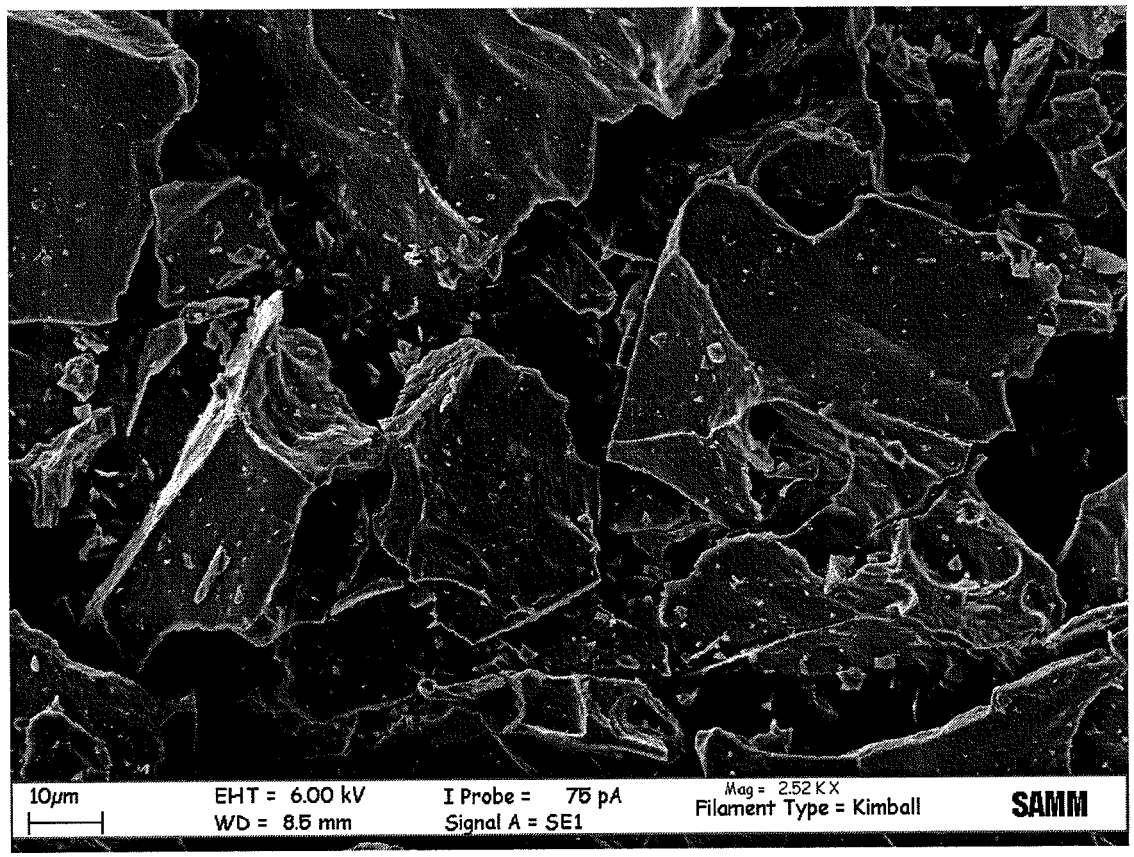
FIG. 2 SEM picture of lyophilized Valgancyclovir hydrochloride.
Figure 3:
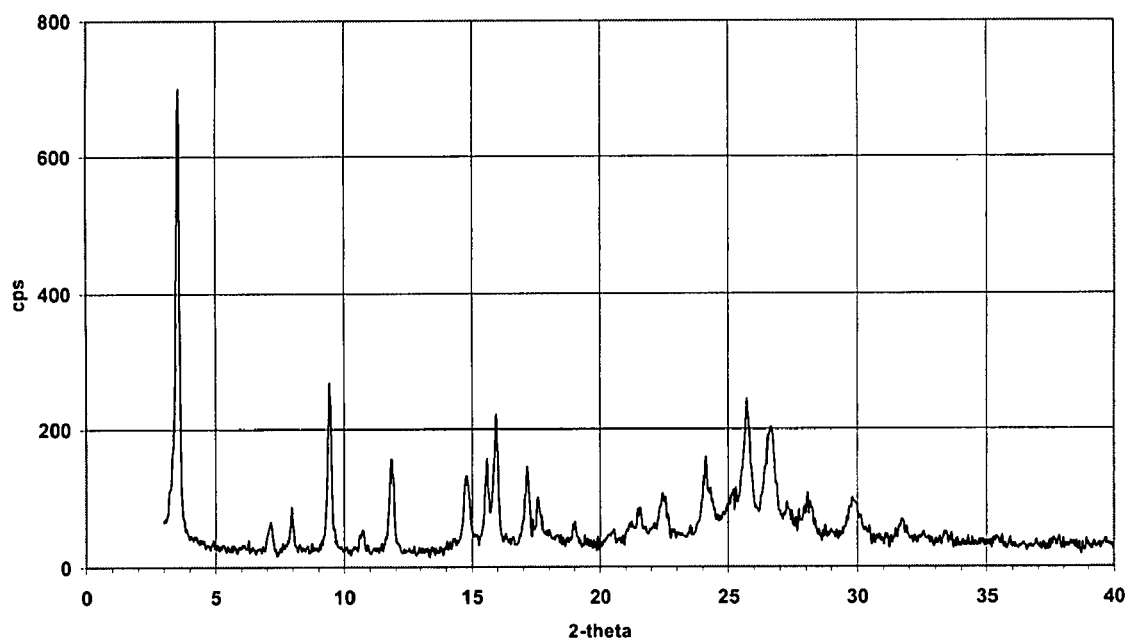
FIG. 3 powder X-ray diffraction pattern of crystalline Valgancyclovir hydrochloride.
Figure 4:
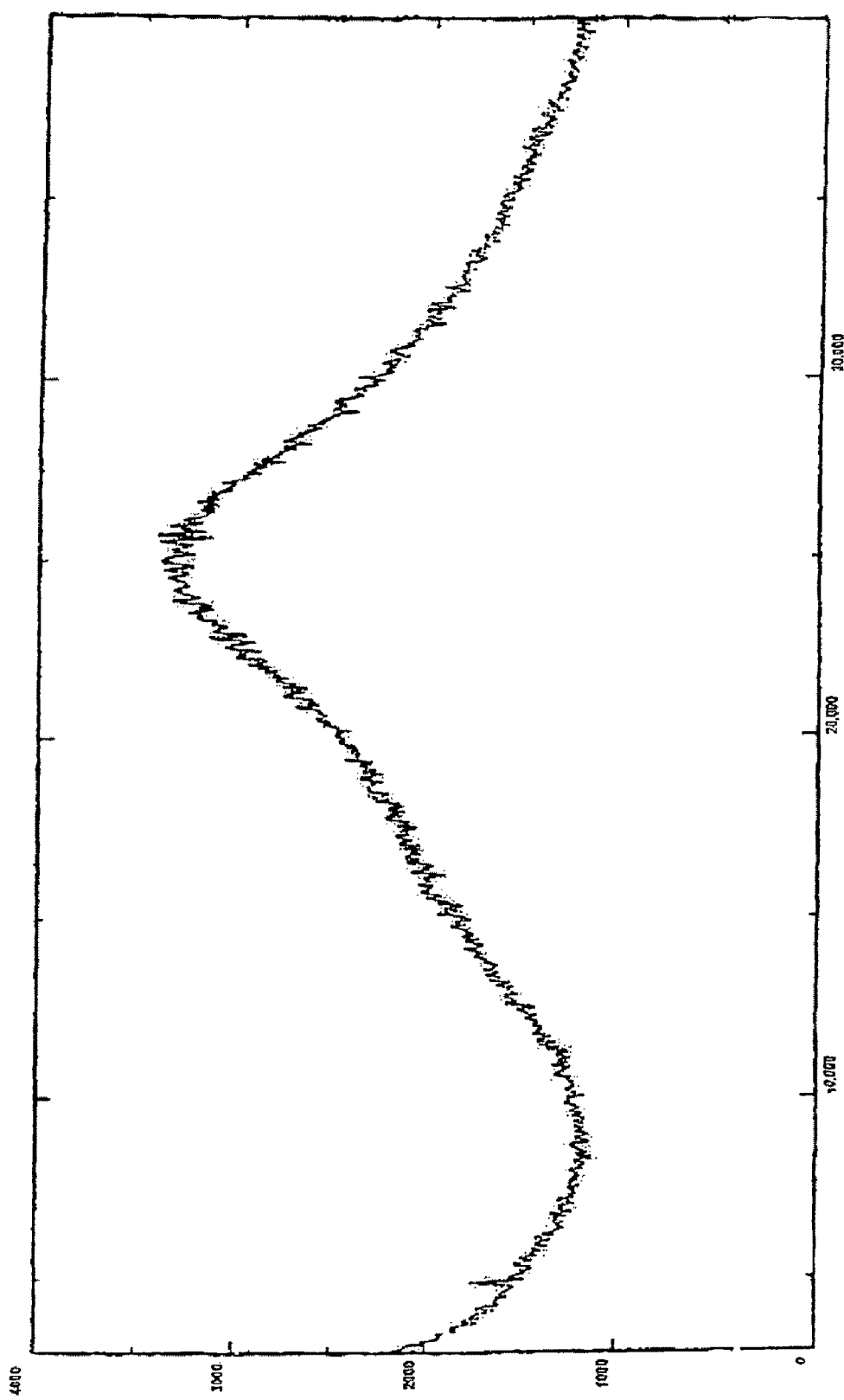
FIG. 4 powder X-ray diffraction pattern of amorphous Valgancyclovir hydrochloride, as disclosed in WO 2005/021549.
Figure 5:
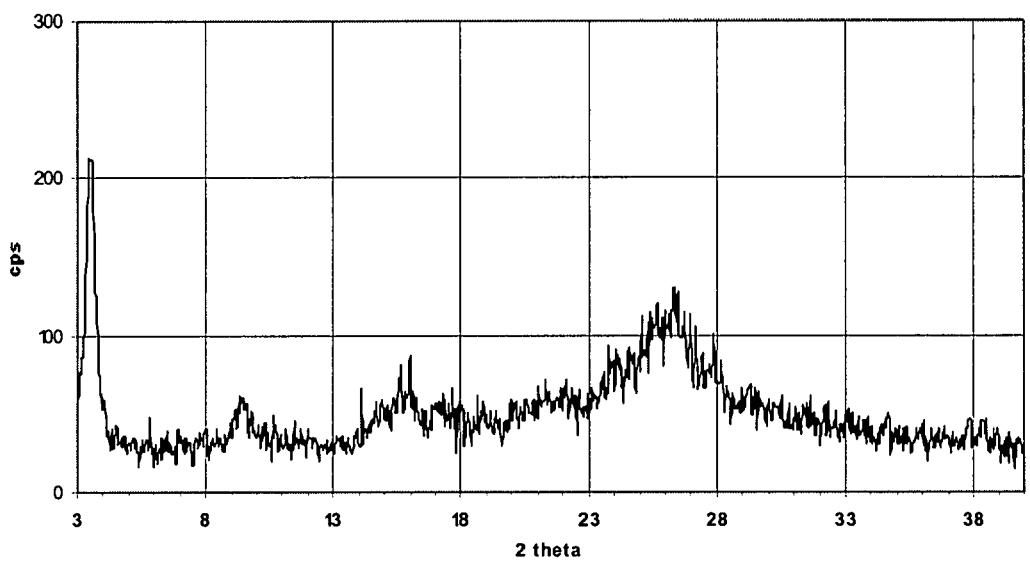
FIG. 5 powder X-ray diffraction pattern of lyophilized Valgancyclovir hydrochloride.
Figure 6:
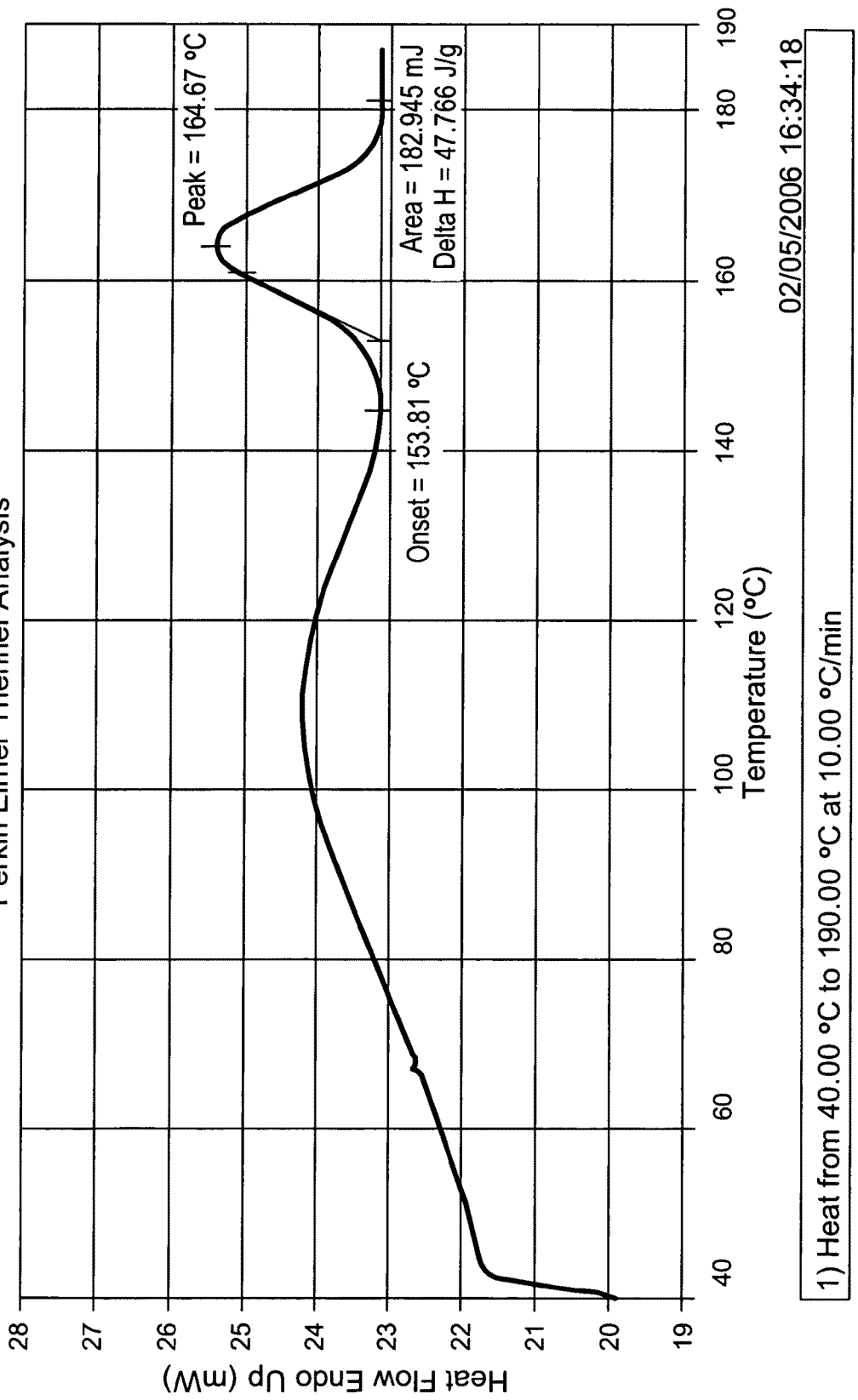
FIG. 6 DSC thermogram of crystalline Valgancyclovir hydrochloride.

The present invention provides a method for the preparation of valgancyclovir hydrochloride by the following Scheme 2

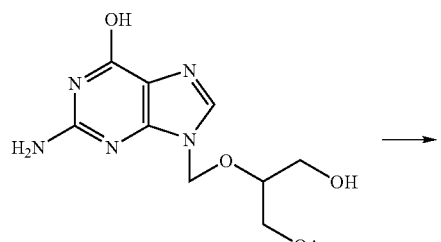

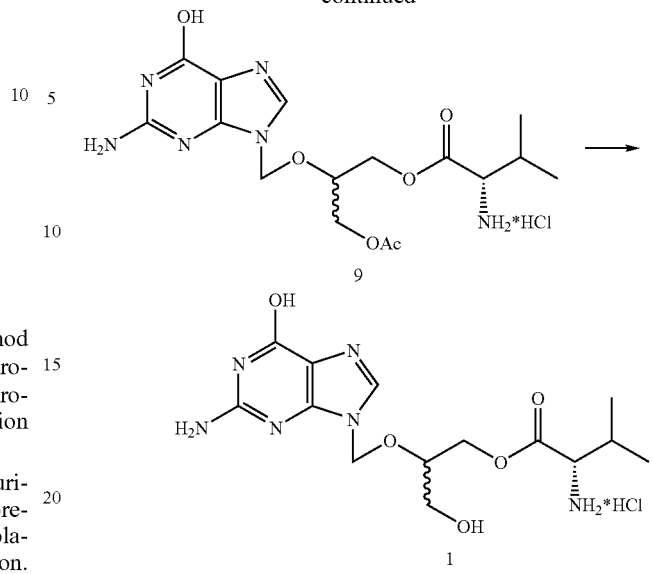

The process comprises:
i) reacting a compound of formula 7 with a compound of formula 8,

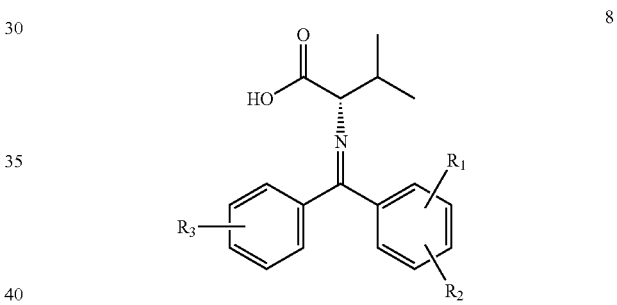

wherein $R_1$, and $R_2$ may be, each independently, hydrogen, a $C_1$-$C_4$ alkyl, a halogen atom, a hydroxyl, or an alkoxy group; $R_3$ may be hydrogen, an alkyl group, or an alkoxy group, and the double bond may either be in the E or Z configuration or a mixture thereof, in a suitable solvent at a suitable temperature in presence of a suitable condensing agent, to afford a compound of formula 9.

Suitable solvents are selected from aprotic solvents, preferably polar aprotic solvents and most preferably tetrahydrofuran, dioxane, formamide, N,N-dimethylformamide, N,N-dimethylacetamide, and the like. Suitable temperatures are in the range from −20° C. to 80° C., preferably from −10° C. to 40° C. and most preferably from −10° C. to 20° C.

Suitable condensing agent are selected from those conventionally used in peptide syntheses or previously used for the preparation of valacyclovir or valgancyclovir, such as dicyclohexylcarbodiimide (DCC), optionally in the presence of 1-hydroxybenzotriazole, N-(3-dimethylaminopropyl)-N'-ethylcarbodiimide (EDC) and its salts such as hydrochloride (EDAC), or similar diimides, like N,N'-diisopropylcarbodiimide (DIC). Other useful condensing agents include (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotrizol-1-yl)-N,N,N',N'-tetramethyluronium hexafluorophosphate (HBTU), and the like.

ii) pouring the reaction mixture in an hydro-alcoholic solution, maintained at a suitable pH, iii) optionally recovering the ketone of formula 10 above by filtration or solvent extraction, and iv) hydrolyzing compound 9 to afford compound of formula 1 in suitable conditions.

Suitable solvents include $C_1$-$C_4$ alcohols or $C_1$-$C_4$ alcohols/water mixtures, preferably $C_1$-$C_3$ alcohols such as methanol or ethanol, in admixture with water, preferably with a water content from 10% up to 50%. Suitable temperatures range from –10° C. to 60° C., preferably from 0° C. to 50° C., and most preferably from 5° C. to 40° C. The reaction time ranges within wide intervals, e.g. from a few minutes to a few days, usually from one hour to 3 days The pH of the reaction medium is usually acidic, i.e. from apparent pH of 3.5-6 to strongly acidic values (i.e. lower than 2).

v) purifying compound 1 by precipitation of gancyclovir, and isolating it by freeze-drying or optionally, according to scheme 3,

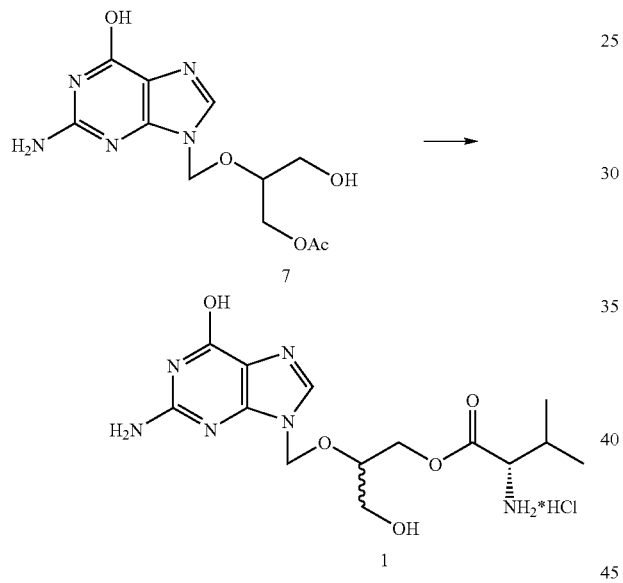

Scheme 3 i) reacting a compound of formula 7 with a compound of formula 8,

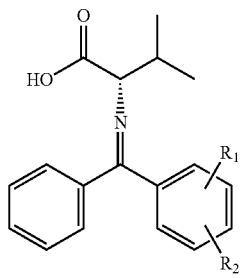

8 wherein $R_1$ and $R_2$ are as defined above and the double bond may either be in the E or Z configuration or a mixture thereof, in a suitable solvent at a suitable temperature in presence of a suitable condensing agent.

Suitable solvents for the reaction above are selected from aprotic solvents, preferably polar aprotic solvents and most preferably tetrahydrofuran, dioxane, formamide, N,N-dimethylformamide, N,N-dimethylacetamide and the like. Suitable temperatures are in the range of –20° C. to 80° C., preferably from –10° C. to 40° C. and most preferably from –10° C. to 20° C. Suitable condensing agent are selected from that conventionally used in peptide syntheses or previously used for the preparation of valacyclovir or valgancyclovir, such as DCC, optionally in the presence of 1-hydroxybenzotriazole, N-(3-dimethylaminopropyl)-N'-ethylcarbodiimide (EDC) and its salts such as hydrochloride (EDAC), or similar diimides, like N,N'-diisopropylcarbodiimide (DIC). Other useful condensing agents include (benzotriazol-1-yloxy)tris (dimethylamino)phosphonium hexafluorophosphate (BOP), (benzotriazol-1-yloxy)tripyrrolidinophosphonium hexafluorophosphate (PyBOP), O-(benzotrizol-1-yl)-N,N,N',N'-tetramethyluronium hexafluorophosphate (HBTU), and the like, ii) pouring the reaction mixture in an hydro-alcoholic solution, maintained at a suitable pH, iii) optionally recovering the ketone of formula 10 above by filtration and iv) recovering valgancyclovir hydrochloride from the solution ii).

Preferably, the solvents in step ii) and iv) are the same.

Suitable solvents include $C_1$-$C_4$ alcohols or $C_1$-$C_4$ alcohols/water mixtures, preferably $C_1$-$C_3$ such as methanol or ethanol, in mixture with water, preferably with a water content in the mixture from 10% up to 50%. Suitable temperatures range from –10° C. to 60° C., preferably from 0° C. to 50° C., most preferably from 5° C. to 40° C. The reaction time ranges within wide intervals, e.g. from a few minutes to a few days, usually from one hour to 3 days. The pH of the reaction medium is usually acidic, i.e. from apparent pH of 3.5-6 to strongly acidic values (i.e. lower than 2).

v) purifying compound 1 by gancyclovir precipitation, and isolating it by lyophilization.

In turn, compounds of formula 8 are prepared according to Scheme 4.

Scheme 4

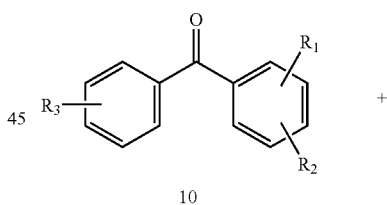

10

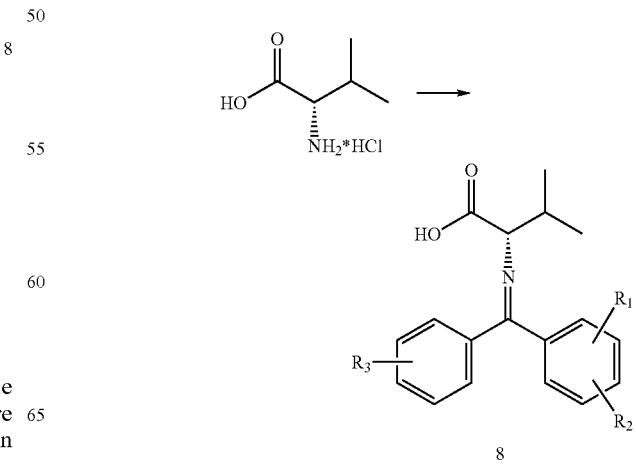

8 wherein $R_1$, $R_2$, and $R_3$ are as defined above, by reaction of L-valine with a ketone of formula 10, wherein $R_1$, $R_2$, and $R_3$ have the same meanings as defined in compounds of formula 8, in a suitable solvent at a suitable temperature. Compounds 8 may be used as a solution or preferably isolated, and the double bond may either be in the E or Z configuration or a mixture thereof.

The following examples further illustrate the invention.

Example 1

L-Valine (10 g), tetramethylammonium hydroxide (25% methanolic solution, 34 g) and 100 ml of ethanol were charged in a 500 ml flask. The mixture was stirred at room temperature till complete solution and about 50 ml ethanol were distilled off. To the resulting mixture, 20 g of 5-chloro-2-hydroxy benzophenone and ethanol (175 ml) were added. The suspension was stirred at room temperature for a few days till complete solution, and the solvent was removed in vacuo. The residue was taken-up with water (150 ml) and extracted with ethyl acetate (3×100 ml). The organic layer was discarded and fresh ethyl acetate (50 ml) was added. The mixture was cooled to about 10° C. and a 20% solution of citric acid in water (38.5 g) was added slowly till pH=5.5. The organic layer was separated and the water phase was extracted with ethyl acetate (3×50 ml). The organic phases were pooled and washed with water, dried over sodium sulphate and evaporated in vacuo to yield the crude title compound as a yellow solid (27 g). The crude was purified by slurry in cyclohexane (40 ml) with stirring. 25 g of the title compound were obtained as a yellow solid.

Example 2

L-valine 2-[(2-amino-1,6-dihydro-6-oxo-9H-purin-9-yl)methoxy]-3-(acettyloxy)propyl ester hydrochloride (Compound 9)

In a three necks bottom flask the compound of the Example 1 (10 g) was dissolved in DMF (36 ml). The solution is cooled to 0-5° C. and HOBT (4.6 g) and a solution of DCC (6.19 g) in DMF (14 ml) were added. Additional DCC in DMF was added after one hour, and after an additional half a hour stirring, monoacetoxygancyclovir (6 g), and DMAP (0.4 g) were added. Upon reaction completion, the suspension was filtered, quenched with a solution of methanol/water/HCl 2N, filtered, washed on the filter and dried. 4 g of the title compound were obtained.

Example 3

L-valine, 2-[(2-amino-1,6-dihydro-6-oxo-9H-purin-9-yl)methoxy]-3-hydroxypropyl ester, hydrochloride 2 g of the compound obtained from Example 2 was dissolved in methanol/water, 2N HCl was added and the resulting solution was kept at 35° C. for about 24 hors. The solution was cooled to room temperature, the pH of the solution was adjusted to 3-4 by addition of triethylamine, then concentrated to a small volume and diluted with isopropanol. The resulting precipitate is filtered to afford 1.5 g of crude valgancyclovir hydrochloride.

The purification of crude valgancyclovir hydrochloride obtained above was performed by dissolving crude valgancyclovir hydrochloride in water, cooling the solution at 5-10° C. and acidifying. The precipitate was filtered-off and the aqueous solution was washed with ethyl acetate, and then treated with isopropanol in two separate additions. The precipitate was filtered and washed on the filter. The wet solid was then taken up in water and charcoal was added to the obtained solution. The suspension was filtered on a celite pad to yield a clear white-yellowish solution. The solution was freeze-dried to yield 1.1 g of valgancyclovir hydrochloride.

Example 4

L-valine, 2-[(2-amino-1,6-dihydro-6-oxo-9H-purin-9-yl)methoxy]-3-hydroxypropyl ester, hydrochloride In a three necks bottom flask the compound of the Example 1 (10 g) was dissolved in DMF (36 ml). The solution is cooled to 0-5° C., HOBT (4.6 g) and a solution of DCC (6.19 g) in DMF (14 ml) were added. Additional DCC in DMF was added after one hour, after an additional half a hour stirring, monoacetoxygancyclovir (6 g) and DMAP (0.4 g) were added. Upon reaction completion, the suspension was quenched with a solution of methanol/water/HCl 2N, heated to 35° C. until complete hydrolysis. The solution was cooled to room temperature, the pH of the solution was corrected to 3-4 by addition of triethylamine, then concentrated to a small volume, and diluted with isopropanol. The resulting precipitate is filtered to afford 1.1 g of crude valgancyclovir hydrochloride.

The invention claimed is:

1. A process for the preparation of valgancyclovir hydrochloride which comprises:

a) reacting a compound of formula 7,

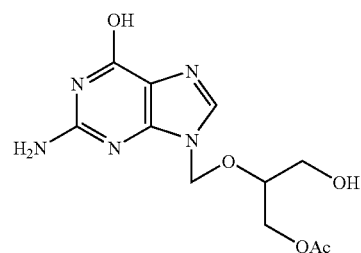

7 in an aprotic solvent, in the presence of a condensing agent, with a compound of formula 8,

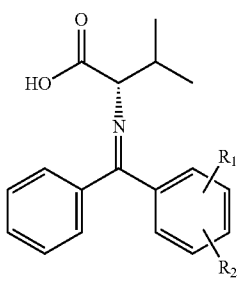

8 wherein $R_1$, and $R_2$ may be, each independently, hydrogen, an halogen atom or an hydroxyl group; the double bond may either be in the E or Z configuration or a mixture thereof to yield a compound of formula 9

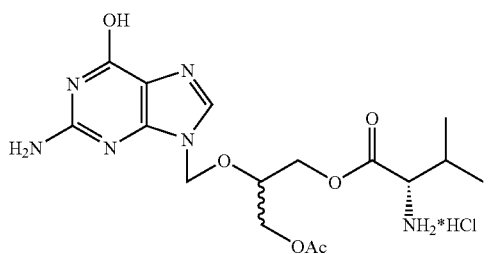

9 b) mild hydrolysis with hydrochloric acid of compound obtained in a) to give valgancyclovir hydrochloride.

2. A process according to claim 1, wherein the aprotic solvent is selected from tetrahydrofuran, dioxane, formamide, N,N-dimethylformamide, N,N-dimethylacetamide.

3. A process according to claim 1 wherein the condensing agent is selected from DCC, optionally in the presence of 1-hydroxybenzotriazole, N-(3-dimethylaminopropyl)-N'-ethylcarbodiimide (EDC) or its hydrochloride salt-(EDAC), or N,N'-diisopropylcarbodiimide (DIC) or (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotrizol-1-yl)-N,N,N',N'-tetramethyluronium hexafluorophosphate (HBTU).

4. A process according to claim 1, further including the isolation of valgancyclovir hydrochloride from the hydrolytic solution by lyophilization.

5. A process according to claim 3 which is effected in the presence of 1-hydroxybenzotriazole, N-(3-dimethylaminopropyl)-N'-ethylcarbodiimide (EDC) or its hydrochloride salt (EDAC), or N,N'-diisopropylcarbodiimide (DIC) or (benzotriazol-1-yloxy)tris(dimethylamino)phosphonium hexafluorophosphate (BOP).

6. A process for producing valgancyclovir hydrochloride which comprises: mild hydrolysis of a compound of formula 9

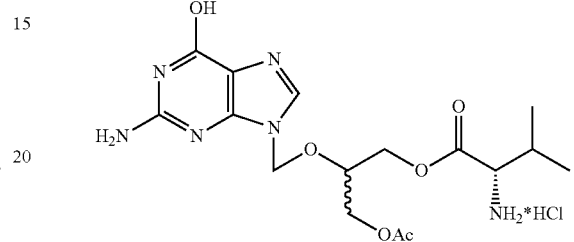

with hydrochloric acid and precipitating gancyclovir from an aqueous solution of the hydrolysis product and isolating pure valgancyclovir hydrochloride by lyophilization.

\* \* \* \* \*